United States Patent
Baker et al.

(10) Patent No.: US 12,329,939 B2
(45) Date of Patent: Jun. 17, 2025

(54) DEVICES FOR RECONSTITUTING AND DELIVERING LYOPHILIZED DRUGS

(71) Applicant: Eli Lilly and Company, Indianapolis, IN (US)

(72) Inventors: Alexander Joseph Baker, Somerville, MA (US); Luke Andrew Gibson, Fishers, IN (US); Hemant Thakorbhai Patel, Indianapolis, IN (US); Ariel Marie Roberts, Greenwood, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 932 days.

(21) Appl. No.: 17/293,289

(22) PCT Filed: Nov. 22, 2019

(86) PCT No.: PCT/US2019/062720
§ 371 (c)(1),
(2) Date: May 12, 2021

(87) PCT Pub. No.: WO2020/112515
PCT Pub. Date: Jun. 4, 2020

(65) Prior Publication Data
US 2021/0393879 A1    Dec. 23, 2021

Related U.S. Application Data

(60) Provisional application No. 62/773,275, filed on Nov. 30, 2018.

(51) Int. Cl.
*A61M 5/20*    (2006.01)
*A61K 9/19*    (2006.01)
(Continued)

(52) U.S. Cl.
CPC .............. *A61M 5/2066* (2013.01); *A61K 9/19* (2013.01); *A61M 5/19* (2013.01); *A61M 5/2033* (2013.01);
(Continued)

(58) Field of Classification Search
CPC .. A61M 5/148; A61M 5/2066; A61M 5/2425; A61M 5/2448; A61M 5/2551;
(Continued)

(56) References Cited

U.S. PATENT DOCUMENTS

| 4,465,488 A | 8/1984 | Richmond et al. |
| 4,608,043 A | 8/1986 | Larkin |

(Continued)

FOREIGN PATENT DOCUMENTS

WO    2014104281    7/2014

OTHER PUBLICATIONS

Patent Cooperation Treaty International Search Report pertaining to International Application No. PCT/US2019/062720; International Filing Date: Nov. 22, 2019; Date of Mailing: Feb. 5, 2020.
(Continued)

*Primary Examiner* — Emily L Schmidt
*Assistant Examiner* — Samuel J Marrison
(74) *Attorney, Agent, or Firm* — Arthur Shum (57) ABSTRACT

The present disclosure relates to drug delivery devices, and in particular, to drug delivery devices configured to reconstitute a lyophilized drug powder into liquid form prior to delivery into a patients body. In some embodiments, such devices include a flexible drug reservoir having a proximal reservoir component storing a liquid diluent and a distal reservoir component storing a lyophilized drug powder, wherein the two compartments are separated by a frangible seal. A compression member may be positioned above the reservoir and held up by a releasable mechanism. When
(Continued)

released, the compression member may be driven downwards to compress the proximal compartment so as to break the frangible seal and allow the diluent to mix with the drug powder and form a liquid drug mixture, and then to eject the liquid drug mixture from the reservoir.

13 Claims, 11 Drawing Sheets (51) Int. Cl.
*A61M 5/19* (2006.01)
*A61M 5/24* (2006.01)

(52) U.S. Cl.
CPC ........ *A61M 5/2425* (2013.01); *A61M 5/2448* (2013.01); *A61M 5/2459* (2013.01); *A61M 2005/2026* (2013.01); *A61M 2005/206* (2013.01); *A61M 2005/2451* (2013.01); *A61M 2202/064* (2013.01); *A61M 2205/3553* (2013.01); *A61M 2205/581* (2013.01); *A61M 2205/587* (2013.01); *A61M 2209/088* (2013.01)

(58) Field of Classification Search
CPC ........... A61M 2005/2451; A61M 2005/14252; A61M 2005/1585; A61M 5/282; A61M 5/14586; A61M 5/14223; A61M 5/14228; A61M 5/14232; A61M 5/16804; A61M 5/16809; F04B 43/02; F04B 43/021; F04B 43/09
See application file for complete search history.

(56) References Cited

U.S. PATENT DOCUMENTS

| | | | |
|---|---|---|---|
| 4,632,244 A | 12/1986 | Landau | |
| 4,731,053 A | 3/1988 | Hoffman | |
| 5,176,634 A | 1/1993 | Smith et al. | |
| 5,209,347 A | 5/1993 | Fabisiewicz et al. | |
| 5,281,202 A * | 1/1994 | Weber | A61M 1/029 222/103 |
| 5,431,496 A | 7/1995 | Balteau et al. | |
| 5,706,937 A | 1/1998 | Futagawa et al. | |
| 6,007,529 A | 12/1999 | Gustafsson et al. | |
| 7,976,526 B2 | 7/2011 | Kitagawa et al. | |
| 8,343,129 B2 | 1/2013 | Falkvall et al. | |
| 8,777,922 B2 | 7/2014 | Inoue et al. | |
| 8,845,611 B2 | 9/2014 | Tsuruoka et al. | |
| 9,737,700 B2 | 8/2017 | Raines | |
| 9,795,773 B2 | 10/2017 | Boyes et al. | |
| 2002/0111580 A1 | 8/2002 | Richeal et al. | |
| 2004/0134802 A1 | 7/2004 | Inoue et al. | |
| 2004/0137177 A1 | 7/2004 | Saito et al. | |
| 2006/0093765 A1 | 5/2006 | Mueller | |
| 2007/0075714 A1 | 4/2007 | Dollinger et al. | |
| 2011/0270220 A1 | 11/2011 | Genosar | |
| 2012/0209183 A1* | 8/2012 | Gray | F04B 43/02 604/131 |
| 2014/0074029 A1* | 3/2014 | Kamen | A61M 5/16831 417/479 |
| 2016/0015890 A1 | 1/2016 | Dassau et al. | |
| 2016/0074586 A1 | 3/2016 | Mernøe | |
| 2017/0224915 A1* | 8/2017 | Destefano | A61M 5/14248 |
| 2017/0246393 A1 | 8/2017 | Genosar | |
| 2018/0133395 A1 | 5/2018 | Margairaz | |
| 2018/0193554 A1* | 7/2018 | Meehan | A61M 5/14248 |
| 2018/0344569 A1* | 12/2018 | Di Naro | F26B 25/063 |

OTHER PUBLICATIONS

Patent Cooperation Treaty Written Opinion of the International Searching Authority pertaining to International Application No. PCT/US2019/062720; International Filing Date: Nov. 22, 2019; Date of Mailing: Feb. 5, 2020.

* cited by examiner

DEVICES FOR RECONSTITUTING AND DELIVERING LYOPHILIZED DRUGS

FIELD OF THE DISCLOSURE

The present disclosure relates to drug delivery devices, and in particular, to drug delivery devices that can reconstitute a lyophilized drug powder into liquid form prior to delivery into a patient's body.

BACKGROUND

Some drugs do not remain stable when in liquid form, and so must be stored in lyophilized form. Such drugs can be delivered either as a powder spray via a patient's nasal passages, or be reconstituted into a liquid form before being injected and/or delivered into the patient's body.

Glucagon is one example of such a drug. Glucagon is a drug generally used by patients with diabetes who are experiencing (or expect to imminently experience) a hypoglycemic event in which their blood or interstitial glucose levels fall below safe levels. If the hypoglycemic event is mild, it can sometimes be treated by having the patient ingest fast-acting carbohydrates. In cases of severe hypoglycemia, however, and/or when the patient is unable to eat or drink, administration of glucagon may be required to bring the patient's glucose levels back up. Since episodes of severe hypoglycemia can occur unexpectedly, patients with diabetes are often encouraged to have a drug delivery device nearby or on their person at all times.

SUMMARY

In one aspect, the present disclosure is directed at a drug-delivery device assembly comprising: a housing having an interior surface, a proximal end, and a distal end; a flexible drug reservoir disposed on the interior surface of the housing, the drug reservoir having a proximal reservoir compartment storing a liquid diluent and a distal reservoir compartment storing a lyophilized drug powder, wherein the proximal reservoir compartment is separated from the distal reservoir compartment by a frangible seal; a releasable mechanism positioned in the housing; a compression member having a proximal end and a distal end and being disposed proximate the drug reservoir, the proximal end of the compression member being attached to a hinge, and the distal end of the compression member being secured by the releasable mechanism; and a biasing member configured to apply pressure to the compression member to bias the distal end of the compression member toward the interior surface of the housing; wherein in response to actuation of the drug-delivery device assembly, the releasable mechanism is configured to release the distal end of the compression member so that the compression member, acting under the pressure from the biasing member, rotates about the hinge to move the distal end of the compression member towards the interior surface of the housing, such that the compression member: compresses the proximal reservoir compartment against the interior surface to force the liquid diluent through the frangible seal and into the distal reservoir compartment, wherein the liquid diluent mixes with the lyophilized drug powder to form a drug mixture, and compresses the distal reservoir compartment against the interior surface to expel the drug mixture from the distal reservoir compartment.

In some embodiments, prior to actuation of the drug-delivery device assembly, a distance between the distal end of the compression member and the interior surface of the housing is greater than a distance between the proximal end of the compression member and the interior surface.

In some embodiments, the lyophilized drug powder is glucagon powder.

In some embodiments, the releasable mechanism comprises one or more pivoting arms.

In some embodiments, the compression member comprises a flat plate.

In some embodiments, the compression member comprises a curved surface.

In some embodiments, the drug-delivery device assembly further comprises an injection needle that is movable between a storage position and an injection position; and an injection spring that applies a biasing force on the needle towards the injection position, wherein the releasable mechanism is further configured to: secure the needle in the storage position when the releasable mechanism holds the distal end of the compression member, and upon releasing the distal end of the compression member, release the needle such that the needle, acting under the biasing force from the injection spring, moves to the injection position.

In some embodiments, the releasable mechanism comprises a needle stop plate coupled to one or more pivoting arms.

In some embodiments, the releasable mechanism is configured to be actuated by at least one of a manual trigger and an electronic trigger.

In some embodiments, the electronic trigger comprises a nitinol wire actuator.

In some embodiments, the releasable mechanism is configured to be actuated upon receipt by the drug-delivery device assembly of a wireless signal from a remote device.

In some embodiments, the drug-delivery device assembly further comprises at least one of a light-emitting diode (LED) and a speaker configured to indicate to a user when the releasable mechanism has been actuated.

In some embodiments, the drug-delivery device assembly further comprises one or more removable adhesive strips configured to secure the housing to a patient's body.

In some embodiments, the drug-delivery device assembly further comprises one or more straps configured to secure the housing to a patient's body.

In some embodiments, in response to actuation of the drug-delivery device assembly, the compression member is configured to compress the proximal reservoir compartment to break the frangible seal prior to compressing the distal reservoir compartment.

BRIEF DESCRIPTION OF THE DRAWINGS

The above mentioned and other features of this present disclosure, and the manner of attaining them, will become more apparent and the invention itself will be better understood by reference to the following description of embodiments of the present disclosure taken in conjunction with the accompanying drawings, wherein.

Corresponding reference characters indicate corresponding parts throughout the several views. Although the exemplifications set out herein illustrates embodiments of the present disclosure, in several forms, the embodiments disclosed below are not intended to be exhaustive or to be construed as limiting the scope of the invention to the precise forms disclosed.

DETAILED DESCRIPTION

The present disclosure relates to drug-delivery devices configured to reconstitute a lyophilized drug powder into liquid form prior to injecting and/or delivering the liquid drug into a patient's body. For ease of explication, this disclosure focuses on drug delivery devices that deliver glucagon. However, the drug-delivery devices disclosed herein may also be configured to deliver lyophilized drugs other than glucagon. For example, the drug-delivery devices disclosed herein may be configured to deliver one or more therapeutic agents including but not limited to glucagon analogs, glucagon derivatives, or any therapeutic agent that may be stored in lyophilized form and that is capable of delivery by the disclosed devices.

Patients in severe hypoglycemic states often pass out or lose consciousness. If the patient passes out, a caregiver (e.g., a nearby friend or loved one) may need to use a drug delivery device to administer glucagon to the patient, even if the caregiver has no prior experience or training with the device. Even if the patient does not pass out, the patient may suffer from limited awareness or dexterity while operating the device. As a result, it would be desirable for drug delivery devices to be easy to use and involve as few manual steps as possible to operate, so that the glucagon can be delivered quickly and easily.

According to some embodiments, the present disclosure relates to drug delivery devices that deliver glucagon that address some or all of the needs discussed above. The disclosed drug delivery devices may have multiple use cases. In one general use case, a drug delivery device that stores a pre-filled dose of glucagon may be secured in contact with a portion of the patient's body. For example, the device may be secured to the patient's arm, abdomen, thigh, or some other portion of the patient's body using adhesive or one or more straps or bands. The patient may wear the device on his or her body during exercise, sleep, or while going about his or her daily activities. While worn, the device may be connected, either via a wired or wireless connection, to a glucose meter such as a blood glucose meter (BGM), continuous glucose meter (CGM), or flash glucose meter (FGM). If the glucose meter indicates that the patient's blood glucose levels are dangerously low, such that the patient is in or is approaching a hypoglycemic state, the delivery device may automatically activate on its own and deliver its pre-stored glucagon. Alternatively, the patient or a nearby caregiver may activate the delivery device on his or her own, either by manually actuating a physical button on the delivery device's exterior housing, or by sending a wireless or wired command signal to the delivery device using an external device, such as a remote controller, a smartphone, or another wearable such as a smartwatch.

In other use cases, the drug delivery device may not be configured to be continuously worn by the patient. In such use cases, the drug delivery device may instead be carried around by the patient or by the patient's caregiver, and be placed in contact with the patient only in an emergency situation when the patient or caregiver perceives that the patient is in or is about to enter a hypoglycemic state. Once placed in contact, the delivery device may be activated to deliver its pre-stored glucagon to the patient. In some cases, the delivery device may be secured in place in such an emergency situation using adhesive or one or more straps or bands—such adhesive, straps, or bands may serve to ensure the device is securely attached to the patient during use, and increase the probability that the needle will sufficiently penetrate the patient's skin to deliver the glucagon.

In some embodiments, the disclosed drug delivery devices may be configured to both be continuously worn by the patient and be placed in contact with the patient only during an emergency situation, depending on the patient's preference. This adaptability allows the disclosed drug delivery devices to be used in multiple situations.

Figure 1:
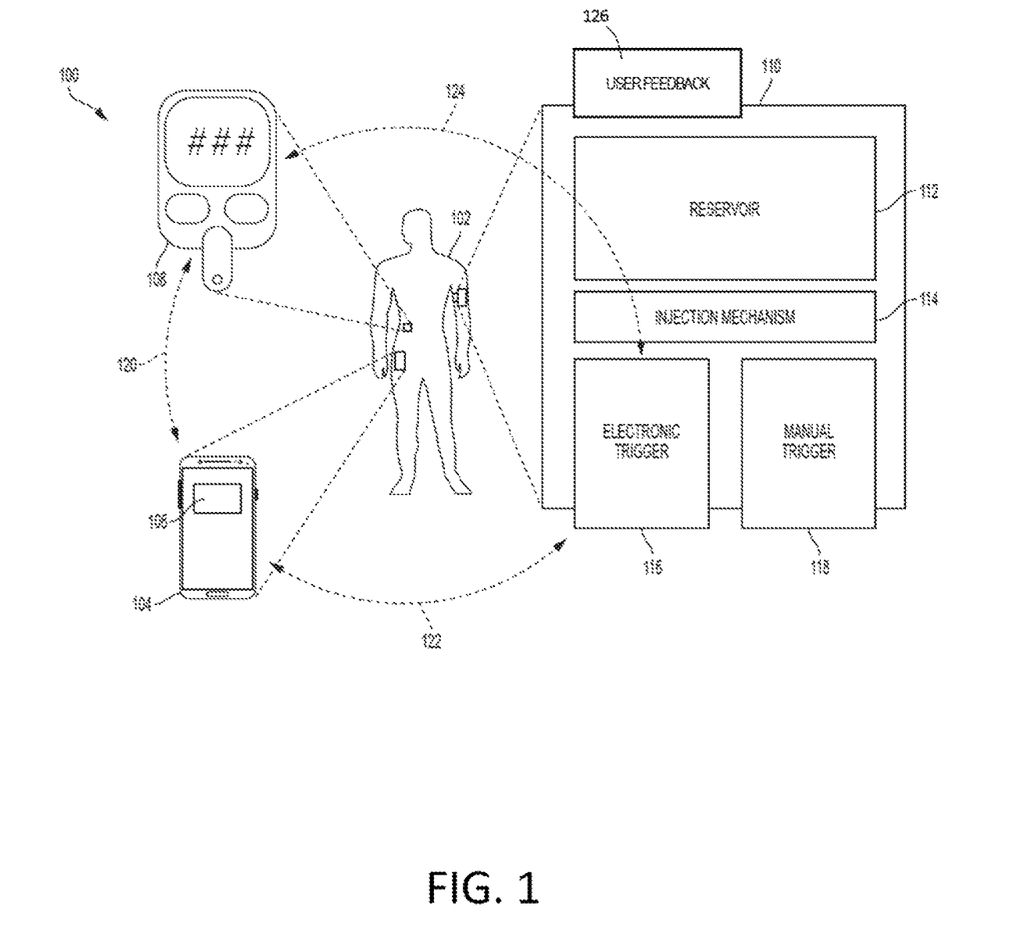
FIG. 1 is a schematic diagram depicting one embodiment of a drug delivery system that comprises a drug delivery device, an optional mobile device, and an optional glucose meter, all associated with a patient.

FIG. 1 shows one embodiment of a drug delivery system 100 that comprises a drug delivery device 110, an optional mobile device 104 implementing a mobile application 106, and an optional glucose meter 108, all associated with a patient 102. The optional mobile device 104 could take the form of any mobile computing device capable of communicating wirelessly with drug delivery device 110 and/or glucose meter 108, and of implementing the mobile application 106—such devices include smartphones, tablets, laptops, or Personal Digital Assistants (PDAs). The optional glucose meter 108 in general could take the form of any device capable of measuring the patient's blood glucose or interstitial glucose levels, such as a blood glucose meter (BGM), a continuous glucose meter (CGM), or a flash glucose meter (FGM). In some embodiments, glucose meter 108 may communicate wirelessly with mobile device 104 over single- or bi-directional link 120. For example, glucose meter 108 may transmit measured glucose levels to mobile device 104, which may display the glucose levels to the patient using mobile application 106.

Figure 9:
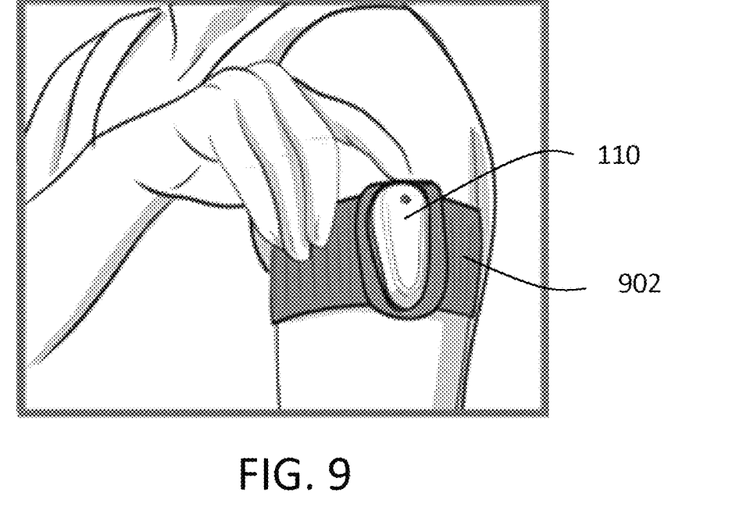
FIG. 9 shows an exemplary way to attach a drug-delivery device assembly to a patient's arm using an arm strap or band.
Figure 10:
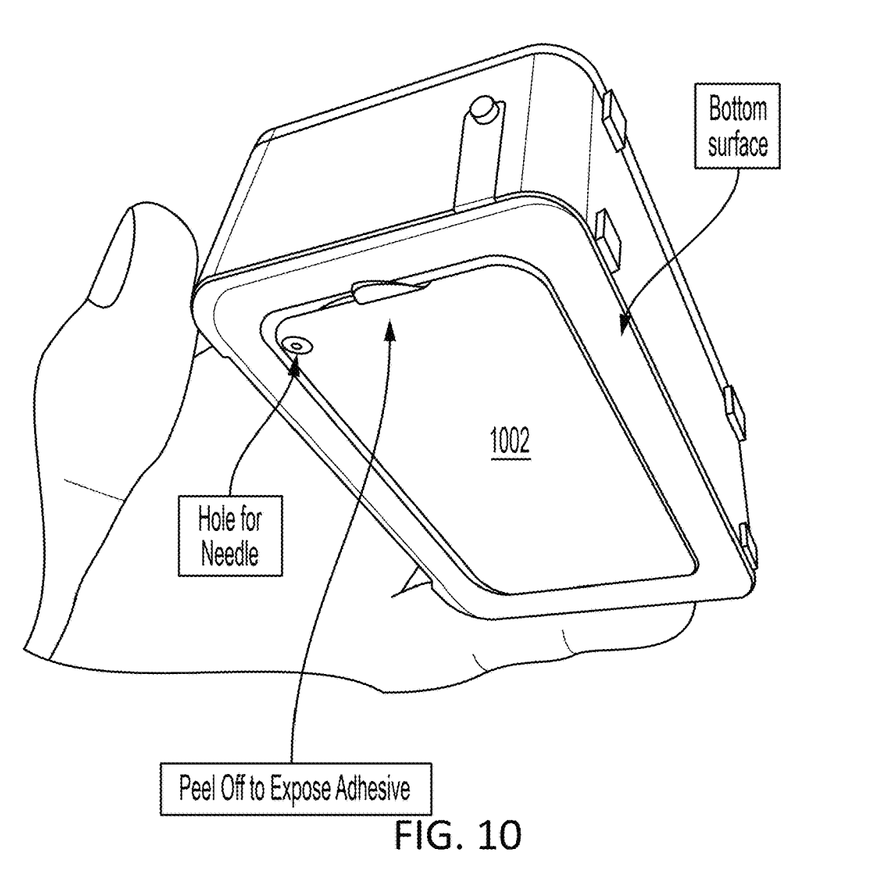
FIG. 10 shows an exemplary adhesive strip disposed on the bottom surface of a drug-delivery device assembly.

As discussed above, drug delivery device 110 may optionally be secured in contact with a portion of patient 102's body—for example, device 110 may be secured to the patient's arm, abdomen, or thigh using adhesive or one or more straps or bands. FIG. 9 depicts one exemplary embodiment in which device 110 is secured to the patient's arm using an arm strap or band 902. In some embodiments, device 110 may be secured to the patient's body using removable adhesive strips. If the device 110 is not activated before it is time to take the device 110 off the patient's body, the adhesive strip may be removed and disposed of The un-activated device 110 may then be re-mounted on the patient's body using a fresh adhesive strip. FIG. 10 depicts another exemplary embodiment in which device 110 is secured to the patient's body using a removable adhesive strip 1002. The strip 1002 may be positioned on the bottom surface of device 110, and provided with a disposable film that, when removed, exposes the adhesive. Strip 1002 may be replaced with a fresh strip as needed.

Device 110 comprises user feedback mechanism 126, which may take the form of one or more light emitting diodes (LEDs), other types of light emitting components, displays, haptic vibration motors, speakers for emitting one or more tones or auditory messages, or some combination of the aforementioned feedback mechanisms. Device 110 also comprises a reservoir 112 configured to store both lyophilized drug powder (for example, but not limited to, lyophilized glucagon powder) as well as a liquid diluent in separate compartments. Injection mechanism 114 comprises the mechanical components and actuators configured to mix the drug powder and the liquid diluent together, and to inject the reconstituted mixture into patient 102's body—these mechanical components and actuators are described in further detail below. Injection mechanism 114 may be triggered by one or both of electronic trigger 116 and manual trigger 118. Manual trigger 118 may comprise a mechanical button or other physical input mechanism on the exterior of device 110 that, when actuated by a user, activates injection mechanism 114. To prevent accidental actuation, the mechanical button may be covered by a shield that slides or hinges open. Electronic trigger 116 may comprise electronic components that activates injection mechanism 114 upon fulfillment of an electronically-determined event, such as expiration of a timer, or a determination that sensed parameters fulfill certain pre-programmed criteria. Device 110 may indicate to a user via user feedback mechanism 126 when injection mechanism 114 has been activated and a dose has been delivered. For example, device 110 may emit a tone, repeated beeps, or other sounds once the injection mechanism 114 has been activated. In some embodiments, these sounds may continue until the full dose has been delivered.

Electronic trigger 116 may also comprise a communication interface configured to communicate wirelessly with one or both of glucose meter 108 (via communication link 124) or mobile device 104 (via communication link 122). Electronic trigger 116 may be configured to activate injection mechanism 114 upon receipt of a wireless signal from either mobile device 104 or glucose meter 108. This wireless signal may comprise an instruction from either mobile device 104 and/or glucose meter 108 to administer glucagon. Alternatively, the wireless signal from mobile device 104 and/or glucose meter 108 may comprise measured glucose levels or other physiological parameters of the patient. When electronic trigger 116 determines that the received glucose levels and/or physiological parameters fulfill certain pre-programmed conditions, electronic trigger 116 may activate injection mechanism 114. In embodiments where the drug powder is glucagon powder, non-limiting examples of such pre-programmed conditions include: (i) if the patient's glucose levels fall below a specified threshold, (ii) if the patient's glucose levels are expected to fall below a specified threshold, (iii) if the patient's glucose levels remain below a specified threshold for a certain length of time, and/or (iv) if the patient's glucose levels fall below a specified threshold and the patient does not respond to an audible, visual, or tactile prompt from mobile device 104. In some cases, electronic trigger 116 may be configured to warn the patient 102 via user feedback mechanism 126 that the device 110 is about to administer the drug using an audible prompt (e.g., an alarm tone), a visual prompt (e.g., flashing lights), and/or a tactile prompt (e.g., a haptic vibration). If the patient does not respond and cancel the proposed administration of drug (e.g., by actuating a button or switch) within a certain period of time (e.g., 10 seconds), electronic trigger 116 may administer the drug. Alternatively, if the patient confirms the proposed drug administration before the period of time has expired (again, for example, by actuating a button or switch), electronic trigger 116 may immediately administer the drug.

Although FIG. 1 illustrates glucose meter 108 and device 110 as separate devices, glucose meter 108 may be integrated with device 110 in some embodiments. If glucose meter 108 is integrated with device 110, the glucose meter 108 may directly communicate the above-mentioned instruction to administer glucagon and/or measured glucose levels to electronic trigger 116 via an internal bus or other circuit connection.

In some embodiments, in addition to electronic trigger 116 and manual trigger 118, the device 110 may comprise one or more buttons or switches that the patient and/or caregiver may actuate to either stop a planned delivery of the drug, or stop an in-progress drug delivery. This button or switch may be separate from the buttons/switches described above for the electronic trigger 116 and manual trigger 118. In some cases, however, one or more of the buttons/switches discussed above for electronic trigger 116 and manual trigger 118 may be repurposed to serve as such a "stop" button when an injection is in-progress.

For delivery devices that deliver therapeutic agents other than glucagon, sensors for measuring physiological parameters other than blood glucose may be used in addition to or in place of glucose meter 108—such measured physiological parameters may include, but are not limited to, blood pressure, blood oxygenation, muscle oxygen saturation, blood pH, heart-rate, EKG, electrical signals from the patient's brain or one or more nerves, patient movement, or body temperature. Electronic trigger 116 may be configured to activate injection mechanism 114 when the sensed physiological parameter(s) fulfill certain criteria, e.g., exceed certain thresholds, exceed certain thresholds for a specified period of time, and/or exhibit undesirable trends.

Figure 2A:
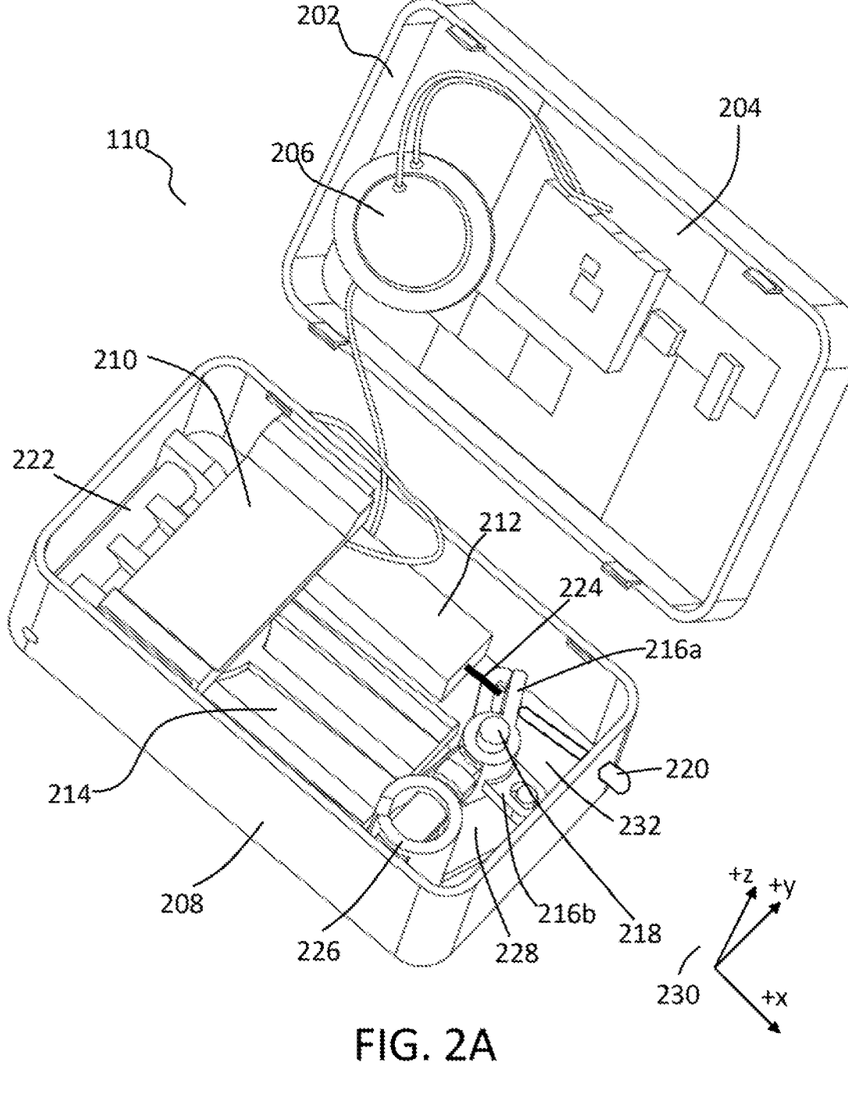
FIG. 2A shows a perspective view of an exemplary drug delivery device in a disassembled state.
Figure 2B:
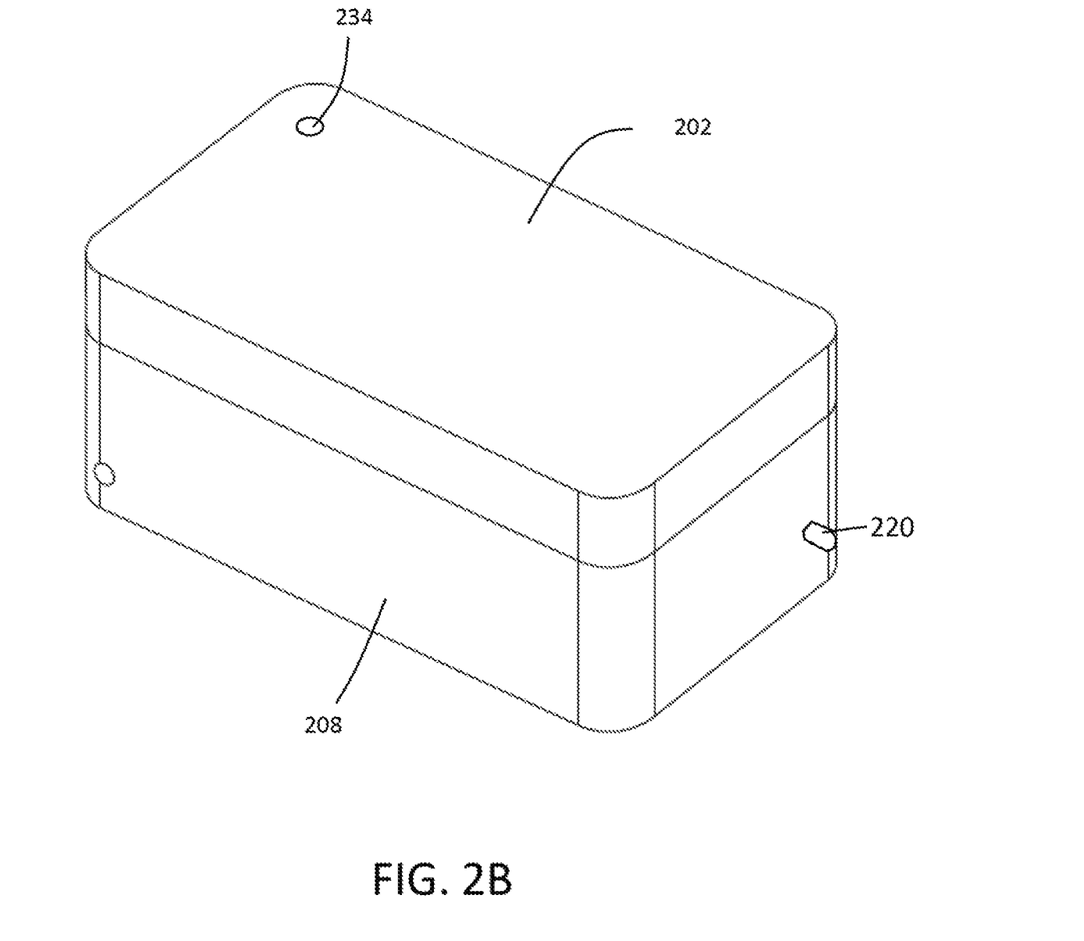
FIG. 2B shows a perspective view of the exemplary drug delivery device of FIG. 2A in an assembled state.
Figure 4A:
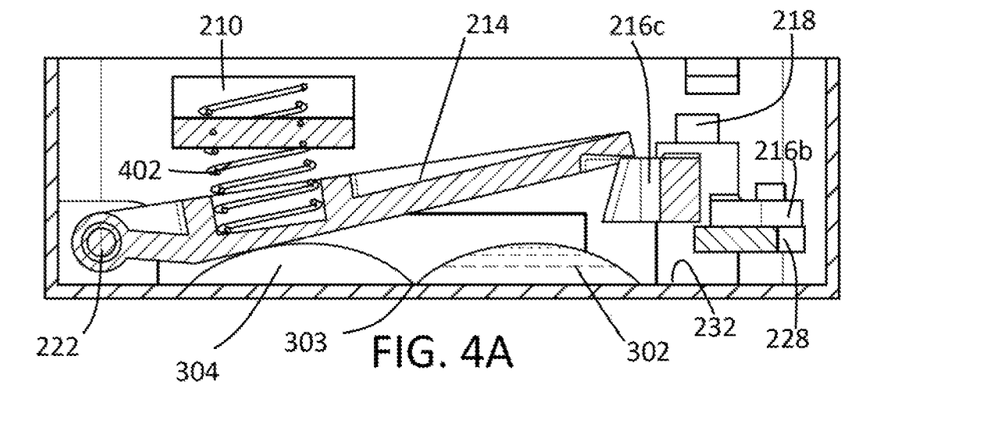
FIG. 4A shows a cutaway profile view of the exemplary drug delivery device of FIG. 2A before being activated.
Figure 4B:
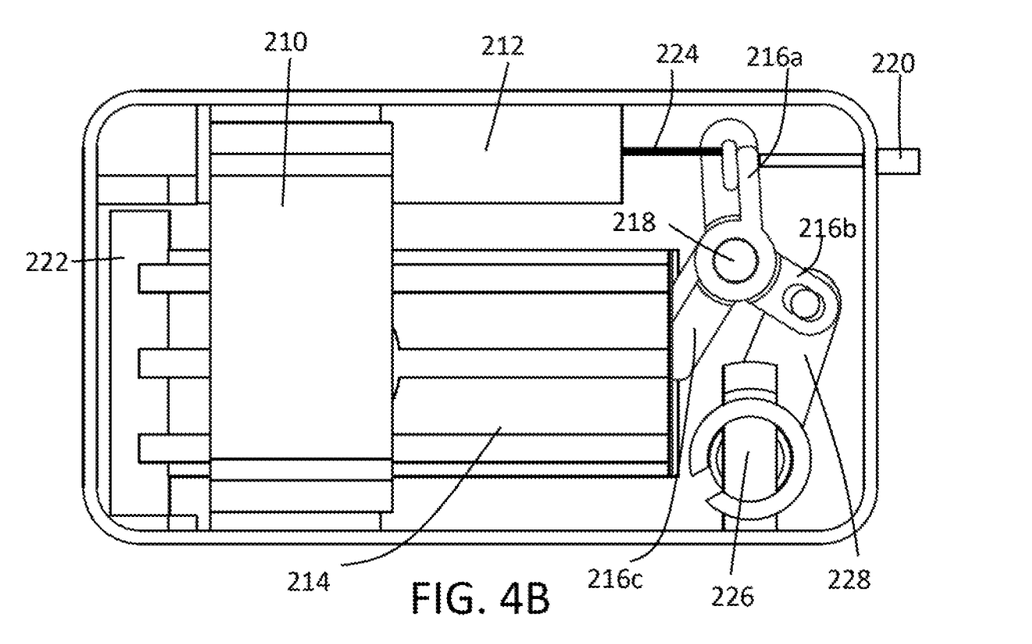
FIG. 4B shows a cutaway top-down view of the exemplary drug delivery device of FIG. 4A.

FIG. 2A shows a perspective view of one embodiment of drug delivery device 110 in a disassembled state, while FIG. 2B shows a perspective view of the same embodiment in an assembled state. FIG. 4A shows a cutaway profile view of the same embodiment, while FIG. 4B shows a top-down view of the same embodiment.

Solely for ease of explication, FIGS. 2A, 2B, and all subsequent figures will use the x, y, z directional system depicted by arrows 230. In the specification and claims, references to the "up," "upward," or "upper" direction shall mean the positive z direction; references to the "down," "downward," or "lower" direction shall mean the negative z direction; references to the "proximal" direction shall mean the negative x direction; references to the "distal" direction shall mean the positive x direction; references to the "left" direction shall mean the positive y direction; and references to the "right" direction shall mean the negative y direction.

According to this exemplary embodiment, device 110 comprises a housing with two portions: an upper housing 202 and a lower housing 208. The two housing components are configured to couple with one another to define an interior volume that houses various components of device 110. As shown in FIG. 2B, the exterior of upper housing 202 may comprise an LED 234 that provides the aforementioned user feedback to the user—for example, the LED 234 may light up when a dose has been delivered. As shown in FIGS. 2A and 4A, the lower housing 208 comprises an interior bottom surface 232 on which some of these components are arranged. Upper housing 202 mounts several components, including a printed circuit board (PCB) 204 comprising control logic operative to perform and/or control the functions described herein. PCB 204 is electronically coupled to a mini speaker or piezo component 206. The mini speaker or piezo component may be used to communicate audible alerts, alarms or information to a user, such as the aforementioned auditory warning that the device is about to administer the drug. The PCB 204 may also be electronically coupled with an antenna configured to communicate wirelessly with optional mobile device 104 and/or optional glucose meter 108. This wireless connection allows device 110 to communicate with mobile device 104 and/or glucose meter 108 as discussed above in FIG. 1. Furthermore, PCB 204 may also be electronically coupled with other user-interface elements to facilitate the user communications discussed above. For instance, PCB 204 may be coupled with one or more additional LEDs or displays to provide the visual prompts and alerts discussed above, a touch-screen and/or keyboard to receive user input, and/or a haptic device to provide the haptic/tactile indications discussed above.

Figure 3A:
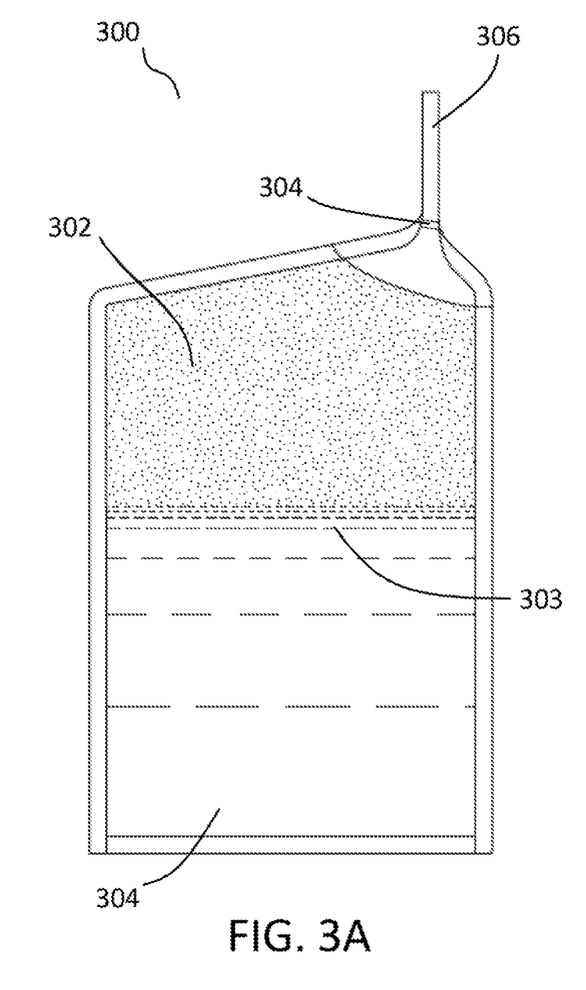
FIG. 3A shows a top-down view of an exemplary two-part drug reservoir.
Figure 3B:
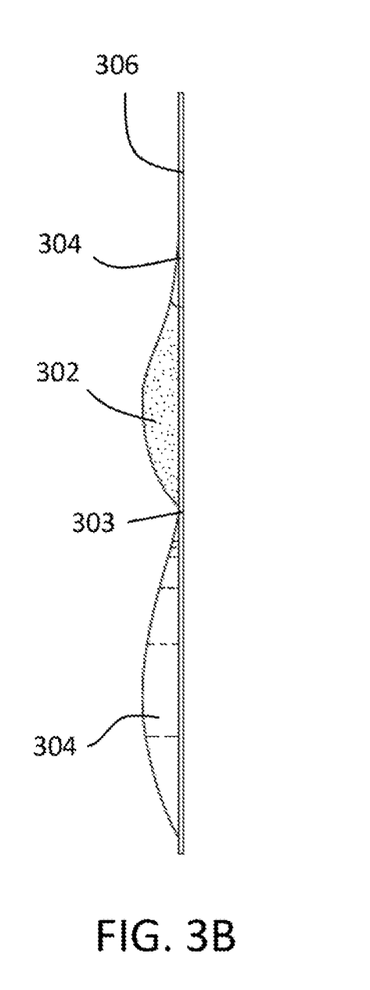
FIG. 3B shows a profile view of the exemplary two-part drug reservoir of FIG. 3A.

Lower housing 208 also mounts several components, including a two-part drug reservoir disposed on interior bottom surface 232. FIGS. 3A and 3B show a top-down and a profile view respectively of an exemplary two-part drug reservoir 300. The reservoir 300 includes a first compartment 304 storing a liquid diluent and a second compartment 302 storing a lyophilized drug powder, such as but not limited to a glucagon powder. The two compartments are separated by a frangible seal 303. A second frangible seal 304 (or a pressure activated valve) separates compartment 302 from fluid conduit 306 and prevents the lyophilized drug powder from escaping into fluid conduit 306 prior to drug delivery. The reservoir 300 is configured such that when the first compartment 304 is compressed, positive pressure generated within the liquid diluent breaks the frangible seal 303, allowing the liquid diluent to mix with the drug powder stored in the second compartment 302. Mixture of the liquid diluent with the drug powder forms a liquid drug mixture. When the second compartment 302 is compressed, positive pressure generated within the liquid drug mixture breaks the second frangible seal 304 (or releases the pressure activated valve) and allows the drug mixture to be expelled from reservoir 300 via fluid conduit 306. As best seen in FIG. 4A, the reservoir 300 is illustratively arranged on interior bottom surface 232 such that the first compartment 304 storing the liquid diluent is closer to the proximal end of device 110, and the second compartment 302 storing the drug powder is closer to the distal end of device 110. As such, compartment 304 is referred to herein as the "proximal" compartment, and compartment 302 is referred to herein as the "distal" compartment.

Also as best seen in FIG. 4A, above reservoir 300 is arranged a compression member 214 that is attached to a hinge 222. In this embodiment, compression member 214 takes the form of a rigid component shaped like a flat plate, and that is configured to rotate about hinge 222. Compression member may be formed out of a unitary piece of plastic, metal, or other rigid material, or may be formed out of the union of multiple components. The lower housing also mounts a pivot support plate 210. Pivot support plate 210 is coupled to or abuts a spring 402, which provides downward pressure on compression member 214.

Lower housing 208 also mounts a pivoting member 216 that rotates about a central spindle 218. As shown in, for example, FIG. 4B, pivoting member 216 comprises three separate arms: 216a, 216b, and 216c. Pivoting member 216 is a rigid component, such that while pivoting member 216 may rotate as a whole about central spindle 218, the three arms 216a, 216b, and 216c remain fixed relative to each other. Arm 216a is attached to a linkage component 224, which may take the form of either a rigid rod (e.g., made of metal or plastic) or a flexible cable or wire. Linkage component 224 is in turn coupled to an actuator 212. When actuator 212 is activated, it pulls on linkage component 224, which causes pivoting member 216 to rotate counter-clockwise about central spindle 218. Arm 216b is coupled to a needle stop plate 228 that interacts with needle insertion mechanism 226, as described in further detail below. In some embodiments, actuator 212 may be a solenoid-based actuator. In other embodiments, actuator 212 may be a nitinol wire actuator that comprises a nitinol wire that changes shape or contracts when an electrical current is run through said wire. Nitinol wire actuators may be an advantageous type of actuator for use in device 110 because of their small size, low profile, and low power requirements.

Rotation of pivoting member 216 accomplishes two functions: it releases compression member 214 so that member 214 can swivel downwards and compress the proximal drug compartment 304 against interior bottom surface 232 (described in further detail below with reference to FIGS. 4A, 4B, 5A, 5B, 6A, and 6B), and it releases a needle within needle insertion mechanism 226 so as to inject the drug into a patient (described in further detail below with reference to FIGS. 7A and 7B). Pivoting member 216 can be rotated in at least two ways. First, pivoting member 216 is rotated by actuator 212 via linkage component 224, as described previously. Actuator 212 may be activated based on an instruction received from PCB 204. As such, PCB 204, actuator 212, and linkage component 224 provides the functionality of electronic trigger 116 described previously. Second, pivoting member 216 is alternatively rotated by pressing on a manual push button 220 (shown in FIG. 2A). In one embodiment, push button 220 is physically linked with pivoting member 216 (e.g., with arm 216a) such that physical actuation of push button 220 causes pivoting member 216 to rotate. FIG. 2A depicts one arrangement in which depression of push button 220 pushes directly on arm 216a; however, push button 220 may be coupled with pivoting member 216 in other ways. For example, the physical linkage between push button 220 and pivoting member 216 may involve multiple intermediate components, such as a gear train or a cable/pulley system (not shown). As such, push button 220 and its interaction with pivoting member 216 provides the functionality of manual trigger 118 described previously. To prevent accidental actuation, push button 220 may be provided with a cover (not shown), such as a shield that slides or hinges open, or a shield that may be removed entirely. Alternatively or in addition, push button 220 may be provided with a lock (not shown) that prevents or blocks push button 220 from being actuated unless the user first actuates a safety catch.

FIGS. 4A, 4B, 5A, 5B, 6A, and 6B show a sequence of steps that illustrate how the two-part drug reservoir 300 (comprising proximal compartment 304 and distal compartment 302) can be compressed to mix and expel the drug therefrom. FIG. 4A shows a cutaway profile view of device 110 before it has been activated when viewed from the right side of the device. FIG. 4B shows a top-down view of device 110 before it has been activated. As previously described, the proximal end of compression member 214 is attached to a hinge 222. Before activation, the distal end of the compression member 214 is held up by arm 216c such that the distal end of the compression member is held further away from the interior bottom surface 232 of the housing than the proximal end of the compression member.

Figures 5A, 5B:
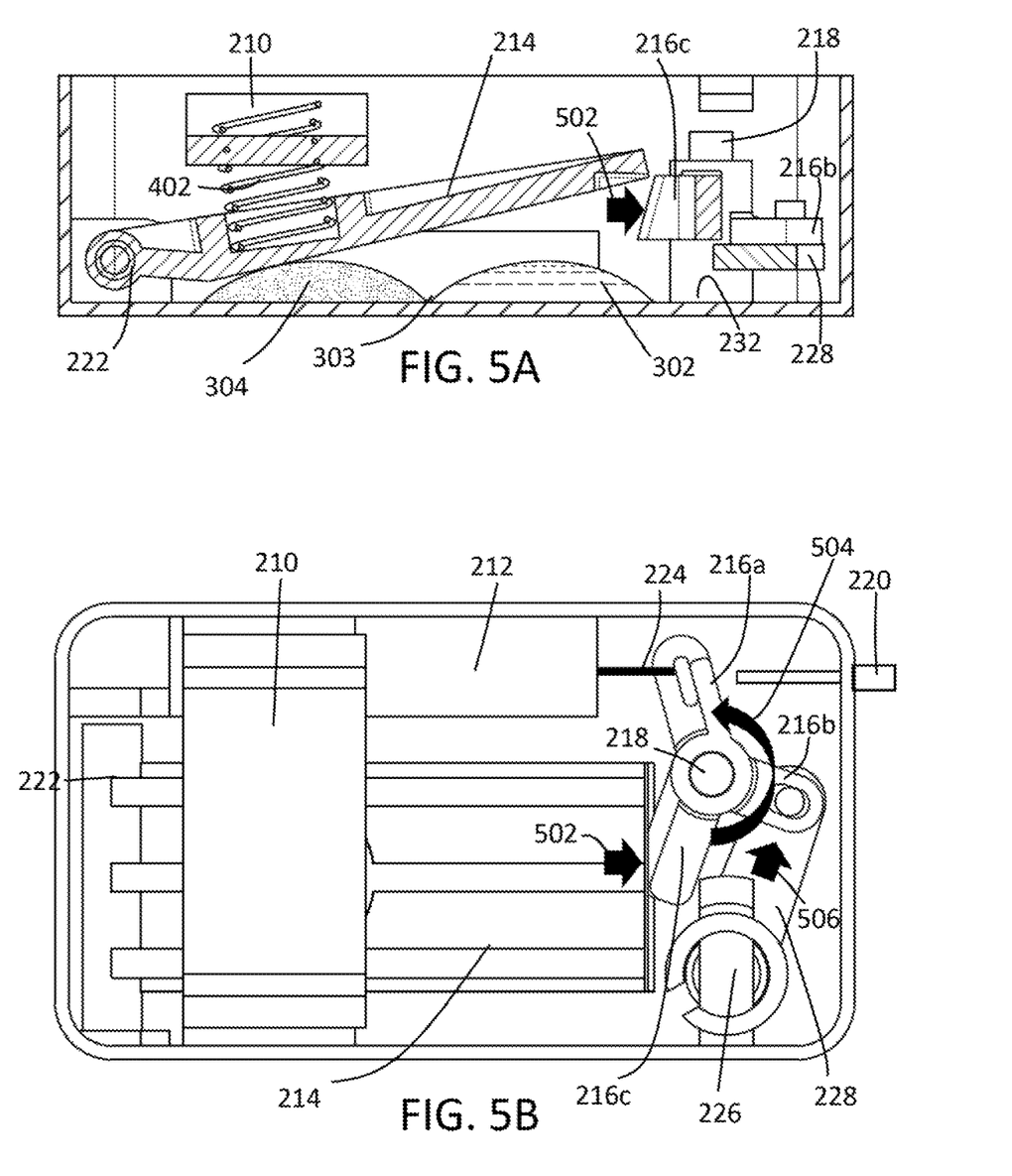
FIG. 5A shows a cutaway profile view of the exemplary drug delivery device of FIG. 2A after being activated but prior to drug delivery.
FIG. 5B shows a cutaway top-down view of the exemplary drug delivery device of FIG. 5A.

FIG. 5A shows a cutaway profile view of device 110 when it has been activated but prior to drug delivery when viewed from the right side of the device. FIG. 5B shows a top-down view of device 110 when it has been activated but prior to drug delivery. Counter-clockwise rotation of pivoting member 216 about central spindle 218 in the direction of arrow 504 activates device 110. As described previously, this rotation can be initiated by actuator 212 and/or manual push button 220. When pivoting member 216 is rotated, arm 216c moves in the direction indicated by arrow 502. This movement of arm 216c releases compression member 214 such that the compression member, acting under the downward pressure from spring 402, rotates downward about hinge 222. This rotation brings the distal end of the compression member 214 down towards the interior bottom surface 232.

Figure 6A:
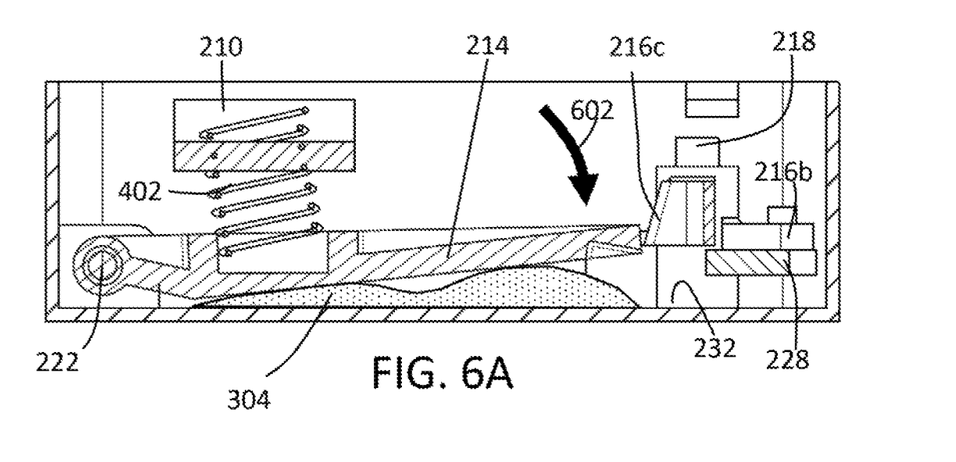
FIG. 6A shows a cutaway profile view of the exemplary drug delivery device of FIG. 2A after being activated and during drug delivery.
Figure 6B:
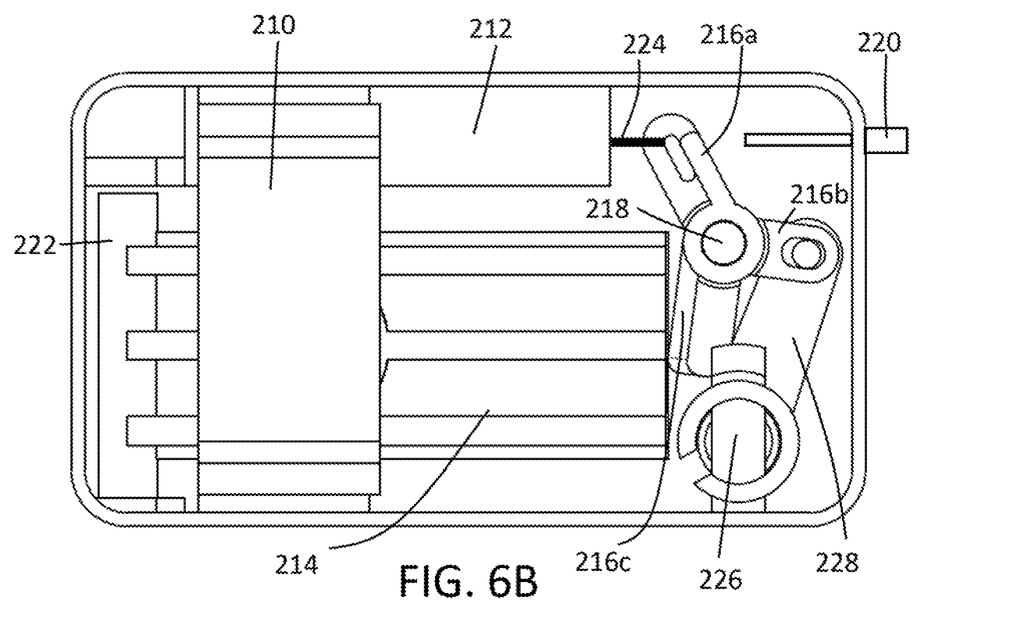
FIG. 6B shows a cutaway top-down view of the exemplary drug delivery device of FIG. 6A.

FIG. 6A shows a cutaway profile view of device 110 after it has been activated and during drug delivery when viewed from the right side of the device. FIG. 6B shows a top-down view of device 110 after it has been activated and during drug delivery. When compression member 214 rotates downward in the direction of arrow 602, it compresses proximal compartment 304 of two-part drug reservoir 300. As previously-described, this compression generates positive pressure within the liquid diluent stored in compartment 304, which breaks the frangible seal 303. Further compression of compartment 304 pushes the liquid diluent into compartment 302, where it mixes with the lyophilized drug powder stored therein to form a liquid drug mixture. As compression member 214 continues to rotate downward, it applies pressure to distal compartment 302, which ejects the liquid drug mixture from the compartment via fluid conduit 306 (not shown in FIGS. 6A and 6B, but illustrated in FIGS. 3A and 3B). Fluid conduit 306 conducts the ejected liquid drug mixture to needle insertion mechanism 226.

Figure 7A:
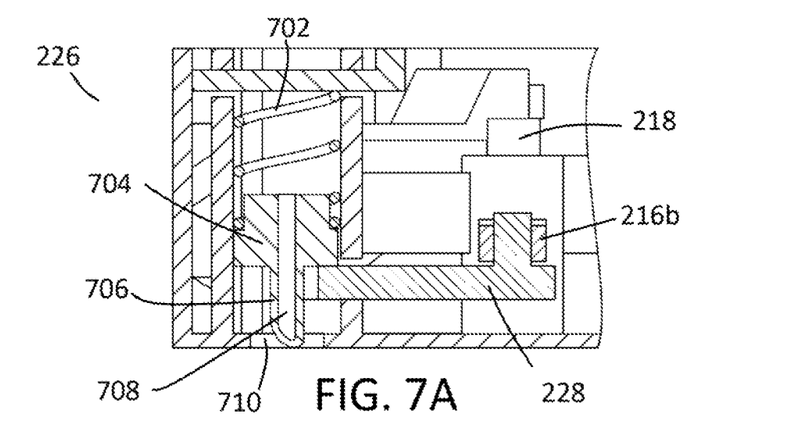
FIG. 7A shows a profile cutaway view of an exemplary needle insertion mechanism before it has been activated.

FIG. 7A shows a profile cutaway view of needle insertion mechanism 226 before activation when viewed from the distal end of device 110. Mechanism 226 comprises a spring 702 that applies downward pressure on a needle plug 704. Needle plug 704 comprises a needle 706, which defines a fluid channel 708. Although needle plug 704 and needle 706 are biased downward by spring 702, both components are prevented from translating downwards by needle stop plate 228. As previously described, needle stop plate is coupled to arm 216b of pivoting member 216.

Figure 7B:
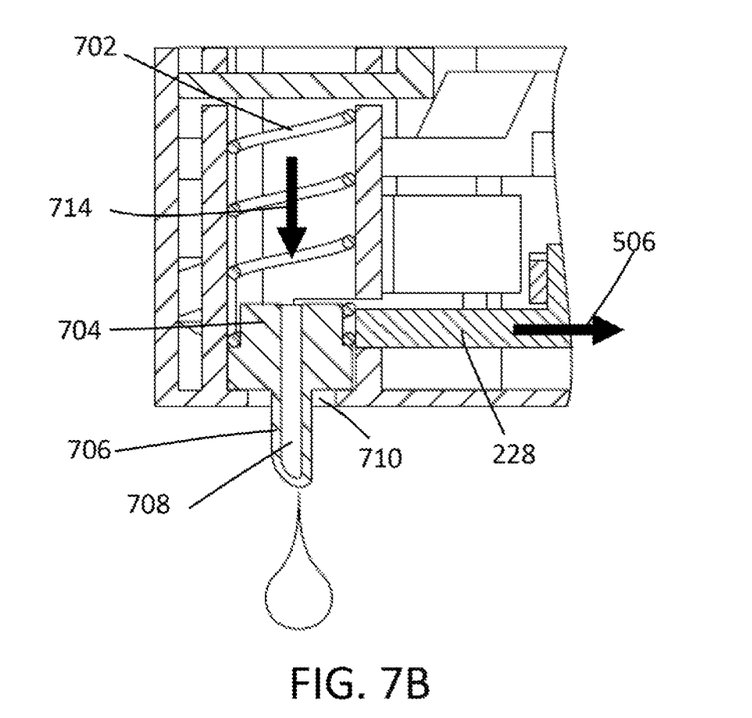
FIG. 7B shows a profile cutaway view of an exemplary needle insertion mechanism after it has been activated.

FIG. 7B shows a similar view of needle insertion mechanism 226 after activation when viewed from the distal end of device 110. As shown in both FIG. 5B (top-down view) and FIG. 7B (profile view), when device 110 is activated and pivoting member 216 rotates counter-clockwise in the direction of arrow 504, needle stop plate 228 is pulled back in the direction of arrow 506 by arm 216b of pivoting member 216. When needle stop plate 228 is pulled back, needle plug 704 and needle 706 are released to be driven downwards by spring 702. When released, needle 706 translates downward and projects through hole 710 defined by the bottom surface of device 110 to inject the patient. Although not shown, fluid channel 708 within needle 706 is connected to drug reservoir 300 by fluid conduit 306, such that the ejected liquid drug mixture travels through needle 706 and into the patient.

Figure 8A:
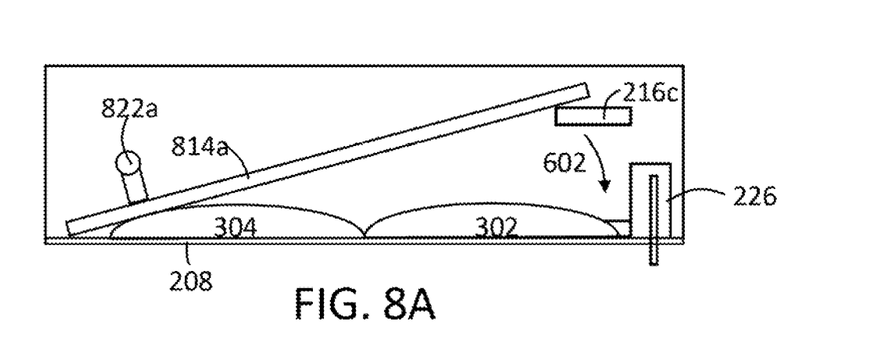
FIGS. 8A, 8B, 8C, 8D, and 8E show alternate, exemplary embodiments of compression members within a drug delivery device.
Figure 8B:
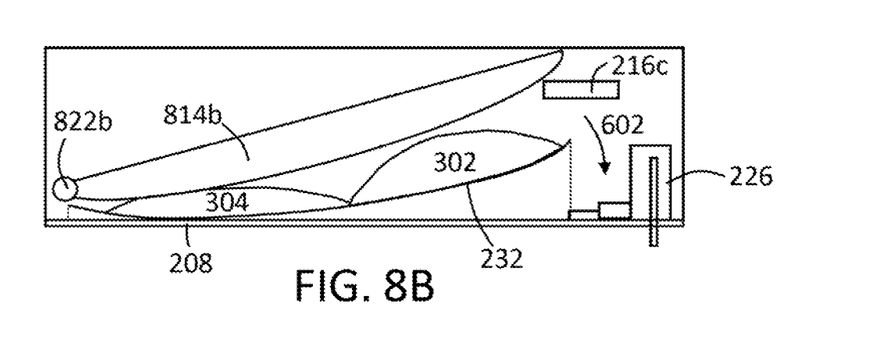
Figure 8C:
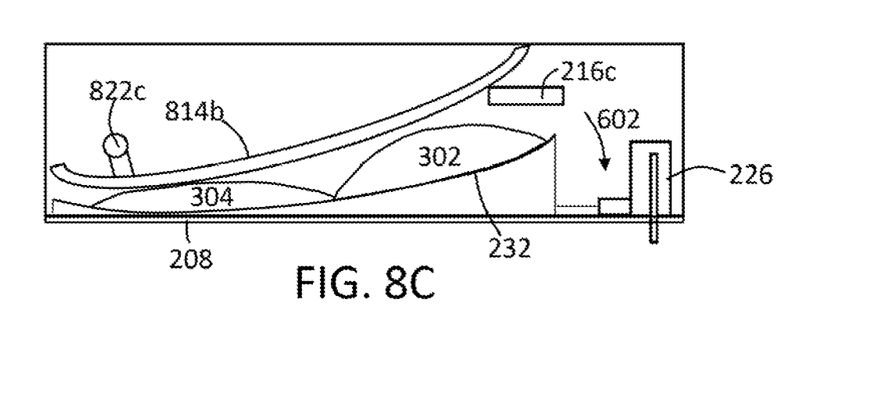

While FIGS. 2A-7B depict one exemplary embodiment of device 110, other embodiments are also possible. For example, FIGS. 2A-7B show that compression member 402 is attached to a hinge 222 at the furthest proximal extent of member 402. However, FIG. 8A shows a simplified representation of another exemplary embodiment in which a compression member 814a is attached to a hinge 822a at a point that is between the furthest proximal extent of member 814a and the midpoint of member 814a. As another example, FIGS. 2A-7B show that compression member 402 is shaped like a substantially flat plate or angled wedge. However, the compression member may also be shaped like a rounded wedge with some flat surfaces and some rounded surfaces (e.g., as depicted by compression member 814b in FIG. 8B), or it may be shaped like a curved plate (e.g., as depicted by compression member 814c in FIG. 8C). If the compression member comprises rounded or angled surfaces, the interior bottom surface 232 may also be contoured to match the curvature or angles of the compression member, as illustrated in FIGS. 8B and 8C. Although not shown in FIGS. 8B and 8C, the expelled medication may be conveyed to needle insertion mechanism 226 via a tube that extends through or around the contoured interior bottom surface 232. Other embodiments may vary both the shape and the compression member and the point of attachment to a hinge. For example, FIG. 8C depicts both a compression member 814b with an alternate shape (a curved plate) and an alternate point of attachment to hinge 822c (e.g., not at the furthest proximal extent of member 814b, but at a point between the furthest proximal extent and the midpoint of member 814b).

Furthermore, while FIGS. 2A-7B depict embodiments in which the compression member is held up by a releasable mechanism that takes the form of pivoting member 216, other suitable releasable mechanisms may alternatively be used. Any releasable mechanism known in the art, and capable of holding up the distal end of the compression member until released by an electronic or manual trigger may be used. For example, pivoting member 216 may comprise more or less than three arms, and/or may comprise as few as one arm. Releasable mechanisms may also pivot or rotate about axes other than the z-axis—for instance, they may pivot or rotate about the x-axis, y-axis, or any other axis in 3D space. In some cases, instead of rotating about a spindle, some releasable mechanisms may take the form of a mechanical catch or latch that opens or closes around a hinge, or that translates along an axis. Yet other releasable mechanisms may involve no moving parts at all—for instance, the releasable mechanism may take the form of a fuse pin that holds or prevents the compression member from moving downwards. The fuse pin may be coupled to PCB 204 such that, when actuated, PCB 204 applies a current to the fuse pin to melt the pin, thus releasing the compression member to move downwards.

Figure 8D:
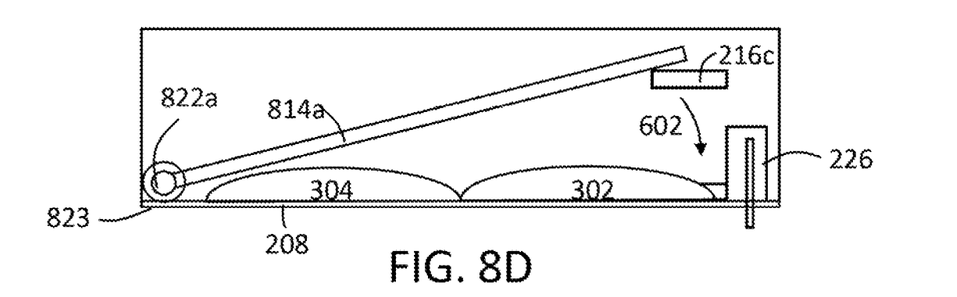

FIG. 8D illustrates another embodiment, in which the compression member is biased downwards by a torsion spring 823 disposed around the hinge 822a at the proximal end of the compression member (e.g., around hinge 222 in FIGS. 4A, 4B, 5A, and 5B). This torsion spring 823 may be provided in addition to or in lieu of compression spring 402. If such a torsion spring is used in lieu of compression spring 402, the pivot support plate 210 may also be eliminated, which may help reduce the overall size of the drug delivery device.

Figure 8E:
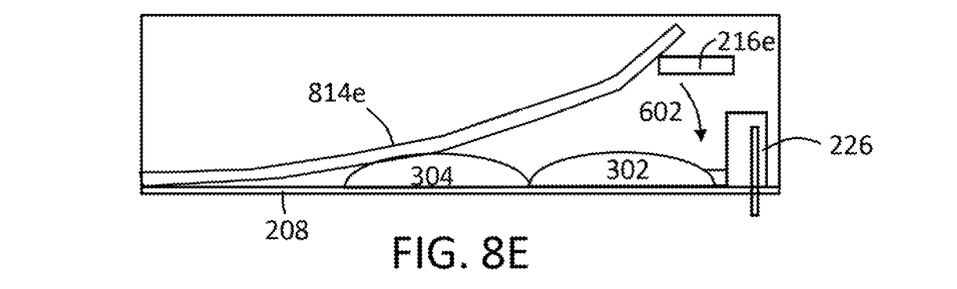

FIG. 8E illustrates yet another embodiment, in which the force that biases the compression member downwards is provided by flexing the compression member itself. For example, the compression member 814e may comprise a sheet of metal or plastic (or other flexible material) that is flexed upward by the releasable mechanism 216e. In such embodiments, the proximal end of the compression member 814e may not be attached to the housing via a pivotable hinge, but instead may be mounted to the lower housing 208 via a rigid, non-pivoting connection. When the releasable mechanism is released, the compression member may be configured to snap downwards as it returns to an un-flexed configuration to dispense the medication as described above. In such embodiments, the compression member would not rotate around a hinge but would return from a flexed state to an un-flexed state to compress the flexible drug reservoir.

While this invention has been described as having an exemplary designs, the embodiments of the present disclosure may be further modified within the spirit and scope of this disclosure. This application is therefore intended to cover any variations, uses, or adaptations of the disclosed embodiments using its general principles.

Various aspects are described in this disclosure, which include, but are not limited to, the following aspects:

1. A drug-delivery device assembly comprising: a housing having an interior surface, a proximal end, and a distal end; a flexible drug reservoir disposed on the interior surface of the housing, the drug reservoir having a proximal reservoir compartment storing a liquid diluent and a distal reservoir compartment storing a lyophilized drug powder, wherein the proximal reservoir compartment is separated from the distal reservoir compartment by a frangible seal; a releasable mechanism positioned in the housing; a compression member having a proximal end and a distal end and being disposed proximate the drug reservoir, the proximal end of the compression member being attached to a hinge, and the distal end of the compression member being secured by the releasable mechanism; and a biasing member configured to apply pressure to the compression member to bias the distal end of the compression member toward the interior surface of the housing; wherein in response to actuation of the drug-delivery device assembly, the releasable mechanism is configured to release the distal end of the compression member so that the compression member, acting under the pressure from the biasing member, rotates about the hinge to move the distal end of the compression member towards the interior surface of the housing, such that the compression member: compresses the proximal reservoir compartment against the interior surface to force the liquid diluent through the frangible seal and into the distal reservoir compartment, wherein the liquid diluent mixes with the lyophilized drug powder to form a drug mixture, and compresses the distal reservoir compartment against the interior surface to expel the drug mixture from the distal reservoir compartment.

2. A drug-delivery device assembly comprising: a housing having an interior surface, a proximal end, and a distal end; a flexible drug reservoir disposed on the interior surface of the housing, the drug reservoir having a proximal reservoir compartment storing a liquid diluent and a distal reservoir compartment storing a lyophilized drug powder, wherein the proximal reservoir compartment is separated from the distal reservoir compartment by a frangible seal; a releasable mechanism positioned in the housing; a compression member comprising a flexible plate having a proximal end and a distal end and being disposed proximate the drug reservoir, the distal end of the compression member being secured by the releasable mechanism above the distal reservoir compartment such that the compression member is held in a flexed state; wherein in response to actuation of the drug-delivery device assembly, the releasable mechanism is configured to release the distal end of the compression member so that the distal end of the compression member moves toward the interior surface of the housing as the compression member returns to an un-flexed state, such that the compression member: compresses the proximal reservoir compartment against the interior surface to force the liquid diluent through the frangible seal and into the distal reservoir compartment, wherein the liquid diluent mixes with the lyophilized drug powder to form a drug mixture; and compresses the distal reservoir compartment against the interior surface to expel the drug mixture from the distal reservoir compartment. The biasing member may comprise a spring that abuts a pivot support plate or a torsion spring disposed around the hinge.

3. The drug-delivery device assembly of any of aspects 1-2, wherein, prior to actuation of the drug-delivery device assembly, a distance between the distal end of the compression member and the interior surface of the housing is greater than a distance between the proximal end of the compression member and the interior surface.

4. The drug-delivery device assembly of any of aspects 1-3, wherein the lyophilized drug powder is glucagon powder.

5. The drug-delivery device assembly of any of aspects 1-4, wherein the releasable mechanism comprises one or more pivoting arms.

6. The drug-delivery device assembly of any of aspects 1-5, wherein the compression member comprises a flat plate.

7. The drug-delivery device assembly of any of aspects 1-6, wherein the compression member comprises a curved surface.

8. The drug-delivery device assembly of any of aspects 1-7, further comprising: an injection needle that is movable between a storage position and an injection position; and an injection spring that applies a biasing force on the needle towards the injection position, wherein the releasable mechanism is further configured to: secure the needle in the storage position when the releasable mechanism holds the distal end of the compression member, and upon releasing the distal end of the compression member, release the needle such that the needle, acting under the biasing force from the injection spring, moves to the injection position.

9. The drug-delivery device assembly of any of aspects 1-8, wherein the releasable mechanism comprises a needle stop plate coupled to one or more pivoting arms.

10. The drug-delivery device assembly of any of aspects 1-9 wherein the releasable mechanism is configured to be actuated by at least one of a manual trigger and an electronic trigger.

11. The drug-delivery device assembly of aspect 10, wherein the electronic trigger comprises a nitinol wire actuator.

12. The drug-delivery device assembly of any of aspects 1-11, wherein the releasable mechanism is configured to be actuated upon receipt by the drug-delivery device assembly of a wireless signal from a remote device.

13. The drug-delivery device assembly of any of aspects 1-12, further comprising at least one of a light-emitting diode (LED) and a speaker configured to indicate to a user when the releasable mechanism has been actuated.

14. The drug-delivery device assembly of any of aspects 1-13, further comprising one or more removable adhesive strips configured to secure the housing to a patient's body.

15. The drug-delivery device assembly of any of aspects 1-14, further comprising one or more straps configured to secure the housing to a patient's body.

16. The drug-delivery device assembly of any of aspects 1-15, wherein, in response to actuation of the drug-delivery device assembly, the compression member is configured to compress the proximal reservoir compartment to break the frangible seal prior to compressing the distal reservoir compartment.

What is claimed is:

1. A drug-delivery device assembly comprising:
a housing having an interior surface, a proximal end, and a distal end;
a flexible drug reservoir disposed on the interior surface of the housing, the drug reservoir having a proximal reservoir compartment storing a liquid diluent and a distal reservoir compartment storing a lyophilized drug powder, wherein the proximal reservoir compartment is separated from the distal reservoir compartment by a frangible seal;
a releasable mechanism positioned in the housing, the releasable mechanism comprising a rigid pivoting member configured to rotate about a central spindle, the rigid pivoting member comprising at least a first arm and a second arm configured to remain fixed relative to the first arm during rotation of the pivoting member;
a compression member having a proximal end and a distal end and being disposed proximate the drug reservoir, the proximal end of the compression member being attached to a hinge, and the distal end of the compression member being secured by the first arm of the pivoting member;
a biasing member configured to apply pressure to the compression member to bias the distal end of the compression member against the first arm of the pivoting member and toward the interior surface of the housing, wherein the distal end of the compression member is prevented from moving toward the interior surface by direct contact with a plane of the first arm of the pivoting member;
an injection needle that is movable between a storage position and an injection position;
an injection spring that applies a biasing force on the needle towards the injection position, wherein the injection needle is prevented from moving towards the injection position by engagement with the second arm of the pivoting member;
wherein in response to actuation of the drug-delivery device assembly, the releasable mechanism is configured to rotate the pivoting member until:
(i) the plane of the first arm of the pivoting member no longer directly contacts the compression member so that the compression member, acting under the pressure from the biasing member, rotates about the hinge to move the distal end of the compression member towards the interior surface of the housing, such that the compression member:
compresses the proximal reservoir compartment against the interior surface to force the liquid diluent through the frangible seal and into the distal reservoir compartment, wherein the liquid diluent mixes with the lyophilized drug powder to form a drug mixture, and
compresses the distal reservoir compartment against the interior surface to expel the drug mixture from the distal reservoir compartment; and
(ii) the second arm of the pivoting member no longer engages the injection needle so that the injection needle, acting under the biasing force from the injection spring, moves to the injection position.

2. The drug-delivery device assembly of claim 1, wherein, prior to actuation of the drug-delivery device assembly, a distance between the distal end of the compression member and the interior surface of the housing is greater than a distance between the proximal end of the compression member and the interior surface.

3. The drug-delivery device assembly of claim 1, wherein the lyophilized drug powder is glucagon powder.

4. The drug-delivery device assembly of claim 1, wherein the compression member comprises a flat plate.

5. The drug-delivery device assembly of claim 1, wherein the compression member comprises a curved surface.

6. The drug-delivery device assembly of claim 1, wherein the releasable mechanism is configured to be actuated by at least one of a manual trigger and an electronic trigger.

7. The drug-delivery device assembly of claim 6, wherein the electronic trigger comprises a nitinol wire actuator.

8. The drug-delivery device assembly of claim 1, wherein the releasable mechanism is configured to be actuated upon receipt by the drug-delivery device assembly of a wireless signal from a remote device.

9. The drug-delivery device assembly of claim 1, further comprising at least one of a light-emitting diode (LED) and a speaker configured to indicate to a user when the releasable mechanism has been actuated.

10. The drug-delivery device assembly of claim 1, further comprising one or more removable adhesive strips configured to secure the housing to a patient's body.

11. The drug-delivery device assembly of claim 1, further comprising one or more straps configured to secure the housing to a patient's body.

12. The drug-delivery device assembly of claim 1, wherein, in response to actuation of the drug-delivery device assembly, the compression member is configured to compress the proximal reservoir compartment to break the frangible seal prior to compressing the distal reservoir compartment.

13. The drug-delivery device assembly of claim 1, wherein the biasing member comprises a spring that abuts a pivot support plate.

* * * * *